US010226556B2

(12) United States Patent
Schroeder et al.

(10) Patent No.: US 10,226,556 B2
(45) Date of Patent: Mar. 12, 2019

(54) APPARATUS FOR EXTRACTING A BLOOD COMPONENT CONTAINED IN A SYSTEM OF BAGS

(71) Applicants: MACO PHARMA, Mouvaux (FR); DELCON S.R.L., Arcore (MB) (IT)

(72) Inventors: Tony Schroeder, Dreieich (DE); Massimo Racanelli, Azzano San Paolo (IT)

(73) Assignees: MACO PHARMA, Mouvaux (FR); DELCON S.R.L., Arcore (MB) (IT)

( * ) Notice: Subject to any disclaimer, the term of this patent is extended or adjusted under 35 U.S.C. 154(b) by 562 days.

(21) Appl. No.: 14/412,780

(22) PCT Filed: Jul. 4, 2013

(86) PCT No.: PCT/FR2013/051592
§ 371 (c)(1),
(2) Date: Jan. 5, 2015

(87) PCT Pub. No.: WO2014/006339
PCT Pub. Date: Jan. 9, 2014

(65) Prior Publication Data
US 2015/0146500 A1 May 28, 2015

(30) Foreign Application Priority Data
Jul. 4, 2012 (FR) .................................. 12 56427

(51) Int. Cl.
*A61M 1/02* (2006.01)
(52) U.S. Cl.
CPC .......... *A61M 1/0209* (2013.01); *A61M 1/025* (2013.01); *A61M 1/0218* (2014.02); *A61M 1/0272* (2013.01); *A61M 2202/0429* (2013.01)

(58) Field of Classification Search
CPC .. A61M 1/0209; A61M 1/025; A61M 1/0218; A61M 1/0254; A61M 1/0272;
(Continued)

(56) References Cited

U.S. PATENT DOCUMENTS 5,690,815 A 11/1997 Krasnoff et al.
5,836,934 A * 11/1998 Beshel ................ A61M 1/0218
210/231

(Continued)

FOREIGN PATENT DOCUMENTS

DE 102007002291 A1 7/2008
EP 1641504 B1 2/2007
(Continued)

*Primary Examiner* — Marc C Howell
(74) *Attorney, Agent, or Firm* — Bachman & LaPointe, P.C.

(57) ABSTRACT

An apparatus for extracting at least one blood component contained in a primary bag of a system of bags, said system of bags comprising at least one bag of solution containing an additive solution for said blood component and at least one collecting satellite bag configured to collect said blood component to which said additive solution has been added, said bags being connected to one another by tubes, said apparatus comprising an extraction device configured to extract the blood component by compressing the primary bag, and a control device configured to transfer said extracted component or of said extracted component and of the additive solution, to the collecting satellite bag by the intermediary of tubes, further comprising: an agitation device, and a drive system, said system being designed to enable the uniform mixing of the extracted blood component and of the additive solution in said collecting satellite bag.

14 Claims, 4 Drawing Sheets

(58) Field of Classification Search
CPC .............. B01F 11/0022; B01F 11/0017; B01F 11/0014; B01F 11/0028
USPC ........................................................ 366/342
See application file for complete search history.

(56) References Cited

U.S. PATENT DOCUMENTS

| | | | | |
|---|---|---|---|---|
| 5,934,804 | A * | 8/1999 | Branson | B01F 11/0014 366/208 |
| 2003/0138349 | A1* | 7/2003 | Robinson | A61M 1/02 422/44 |
| 2006/0013063 | A1* | 1/2006 | Singh | B01F 11/0017 366/239 |
| 2009/0211989 | A1* | 8/2009 | Nguyen | A61K 35/16 210/767 |
| 2013/0256576 | A1* | 10/2013 | Deverre | A61M 39/221 251/215 |
| 2013/0316446 | A1* | 11/2013 | Andersson | C12M 23/14 435/305.1 |

FOREIGN PATENT DOCUMENTS

| | | | | |
|---|---|---|---|---|
| FR | 2968568 A1 * | 6/2012 | .......... | A61M 39/221 |
| WO | WO 0066706 A1 * | 11/2000 | .......... | B01F 11/0017 |
| WO | WO-0066706 A1 * | 11/2000 | .......... | B01F 11/0017 |
| WO | WO 2014033564 A1 * | 3/2014 | .......... | B01F 11/0028 |

\* cited by examiner

APPARATUS FOR EXTRACTING A BLOOD COMPONENT CONTAINED IN A SYSTEM OF BAGS

BACKGROUND

The invention relates to an apparatus for extracting a blood component contained in a primary bag of a system of bags, as well as a method carried out using such an apparatus.

The invention applies to the field of blood transfusion, in particular in the treatment of blood, and notably the separation of blood components.

Whole blood is constituted of two types of components: blood cells comprising red blood cells, white blood cells and the platelets, and plasma wherein the blood cells are in suspension. Currently, only the blood components required for patients are transfused.

Today, in transfusion centers or hospitals, these various blood components are separated via centrifugation: the whole blood from a donor is collected in a bag referred to as the primary bag of a system of bags. Then, the system of bags is placed in a centrifuge in order to separate the various components. There are two types of centrifugation. The centrifugation referred to as gentle of the whole blood results in separating it into two layers: a lower layer rich in red blood cells called packed red blood cells (PRBC); and an upper layer containing plasma, platelets and white blood cells called platelet-rich plasma (PRP). Centrifugation referred to as hard results in a separation into three layers: a lower layer of PRBC; an upper layer of platelet-poor plasma (PPP); and an intermediate layer formed substantially of white blood cells and of platelets, referred to as the white blood cell-platelet layer or buffy coat.

The primary bag containing the components separated by centrifugation is then placed in an apparatus for separating components by compressing the primary bag, in such a way that, for example, the plasma is sent, via a tube, into a first satellite bag. An additive solution of the SAGM (saline—adenine—glucose—mannitol) type is moreover added to the extracted packed red blood cells in order to be able to store them up to 42 days.

An example of an apparatus for separating blood components is for example described in document EP 1 641 504. This separation apparatus is in particular provided with welding-clamps for quasi-automatic operation. However, with this type of apparatus, the operator must still manually break the circuit-openers of the system of bags. Furthermore, this apparatus does not make it possible to obtain a uniform mixture of the packed red blood cells and of additive solution.

However, it is also known that white blood cells have very substantial undesirable effects, which has led to seeking to eliminate them from blood components intended for transfusion. As such, the mixture of the packed red blood cells and of the additive solution is filtered through a white blood cell filter in order to eliminate the highest number of white blood cells as possible. But, if the mixture is not uniform, the filtration risks not being effective.

It is also known in documents DE 10 2007 002 291 and U.S. Pat. No. 5,836,934, apparatuses for separating and filtering blood components via compression. In these systems, the packed red blood cells and the additive solution are sent into a common tube, then the packed red blood cells to which an additive solution has been added is filtered and collected in a storage bag for red blood cells. These addition and mixing systems, although sufficient for carrying out filtration of the packed red blood cells in line under pressure, are not satisfactory in terms of mixing, when the packed red blood cells must be filtered via gravity.

SUMMARY

The invention proposes an entirely automated apparatus enabling in particular the extraction and the uniform mixing of a packed red blood cells and of the additive solution thereof, in order to enable an optimum filtration of the packed red blood cells.

To this effect, according to a first aspect, the invention relates to an apparatus for extracting at least one blood component contained in a primary bag of a system of bags, said system of bags further comprising at least one bag of solution containing an additive solution for said blood component and at least one collecting satellite bag intended for collecting said blood component to which said additive solution has been added, said bags being connected to one another by tubes, said apparatus comprising:
 an extraction device intended for extracting the blood component by compressing the primary bag,
 a control device intended for enabling the transfer of said extracted component or of said extracted component and of the additive solution to the collecting satellite bag by the intermediary of tubes,
 an agitation device intended for agitating the collecting satellite bag, and
 a drive system for commanding said extraction device, said control device and said agitation device, said system being designed to enable the uniform mixing of the extracted blood component and of the additive solution in said collecting satellite bag.

According to a second aspect, the invention relates to a method for extracting at least one blood component contained in a primary bag of a system of bags, using an apparatus according to the first aspect of the invention, said method comprising the steps of:
 compressing the primary bag in such a way as to extract the blood component from the primary bag and transfer it to the collecting satellite bag,
 transferring the additive solution from the bag of solution to the collecting satellite bag during the transfer of the extracted blood component to said collecting satellite bag,
 agitating the collecting satellite bag during the transfer of the extracted blood component and of the additive solution to said collecting satellite bag.

BRIEF DESCRIPTION OF THE DRAWINGS

Other objects and advantages shall appear in the following description.

DETAILED DESCRIPTION

During a donation of blood, the blood is collected in a system of bags comprising several bags connected to one another by tubes.

Figure 1:
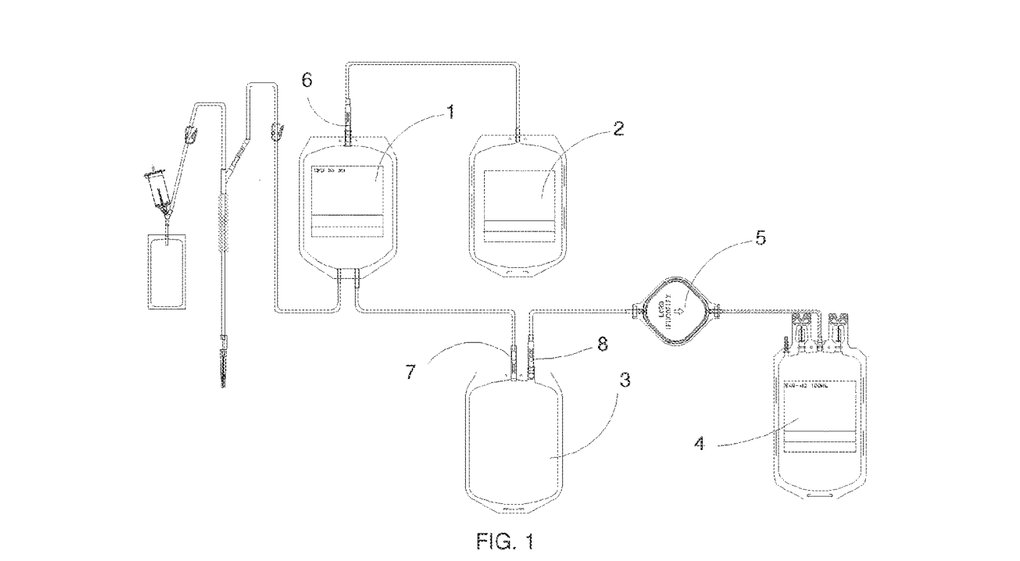
FIG. 1 diagrammatically shows a particular system of bags used with an apparatus according to the invention.

Such a system of bags is for example shown in FIG. 1 and comprises a primary bag 1 intended for collecting the blood from the donor, a satellite bag 2 for collecting plasma, a satellite bag 3 for collecting packed red blood cells, and a bag of solution 4 containing an additive solution. Such a solution is for example the SAGM (saline-adenine-glucose-mannitol) solution that makes it possible to store the packed red blood cells up to 42 days. The primary bag 1 also contains an anticoagulant of the CPD (Citrate Phosphate Dextrose) or ACD (Acid Citrate Dextrose) type.

According to FIG. 1, the system of bags further comprises a filtration unit 5 for removing the white blood cells from the packed red blood cells. Such a filtration unit is for example described in document EP 1 336 417.

The various bags are connected to one another by tubes. Closing elements 6, 7, 8 comprising a weak zone, also referred to as circuit-openers, are housed in the tubes, in the vicinity of the access channels of the bags. These closing elements prevent the flow of fluids in the tubes until the breaking of the weak zone. Such closing elements are described for example in document WO-93/17734. A device for automatically breaking these closing elements is described in document FR 2 968 568.

In practice, after having collected the blood in the primary bag of such a system of bags, this system of bags is placed in a centrifuge in order to separate the various blood components.

After centrifugation, the primary bag 1 contains the various layers of blood components, namely a layer of plasma, a layer of packed red blood cells and possibly a buffy coat.

In order to extract these different blood components in the appropriate bags 2, 3, a separation apparatus is used, which, after manual breaking of the closing elements 6, 7, 8 of the tubes, automatically transfers via an extraction device by compressing the various blood components in the dedicated bags 2, 3.

The invention relates to such an apparatus intended for extracting at least one blood component contained in a primary bag 1 of a system of bags, said system of bags comprising at least one bag of solution 4 containing an additive solution for said blood component and at least one collecting satellite bag 3 intended for collecting said blood component to which said additive solution has been added, said bags 1, 3, 4 being connected to one another by tubes.

The blood component is in particular a packed red blood cells, a plasma or a platelet concentrate or a pool of platelet concentrates. In this case, the additive solution is in particular a preservation solution. An example of a preservation solution for platelets is the SSP+ solution from Maco Pharma (France). Alternatively, the additive solution is a solution that contains an agent to deactivate the pathogens of the blood.

Figure 2:
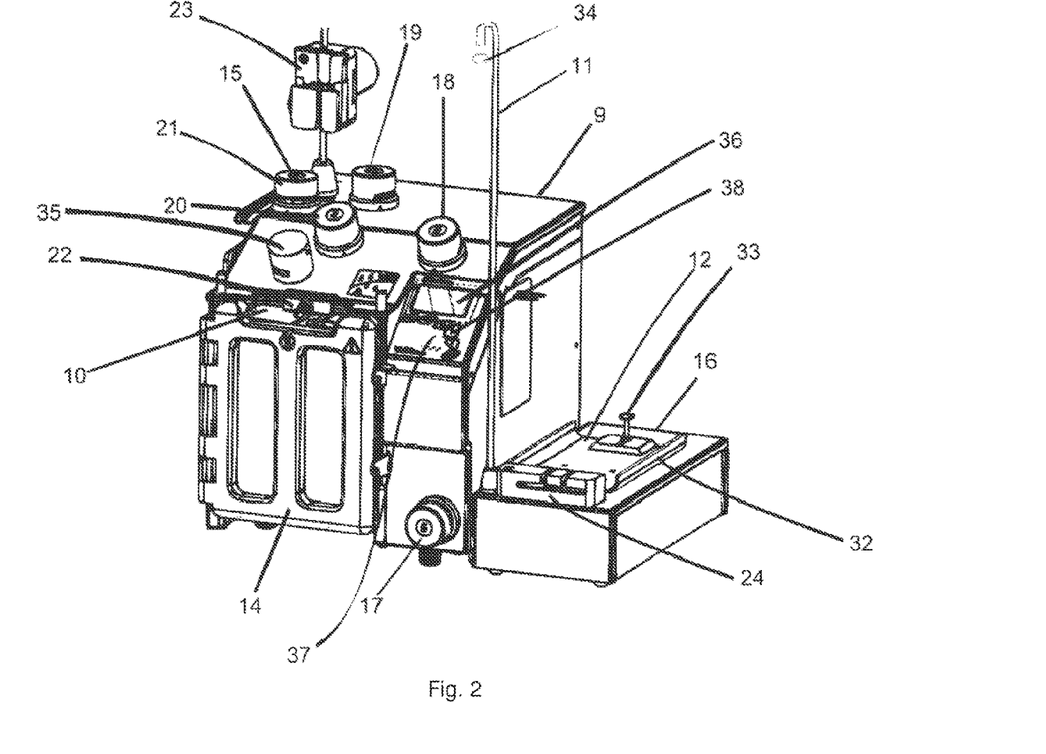
FIG. 2 diagrammatically shows a perspective view of a first embodiment of an apparatus according to the invention.
Figure 3:
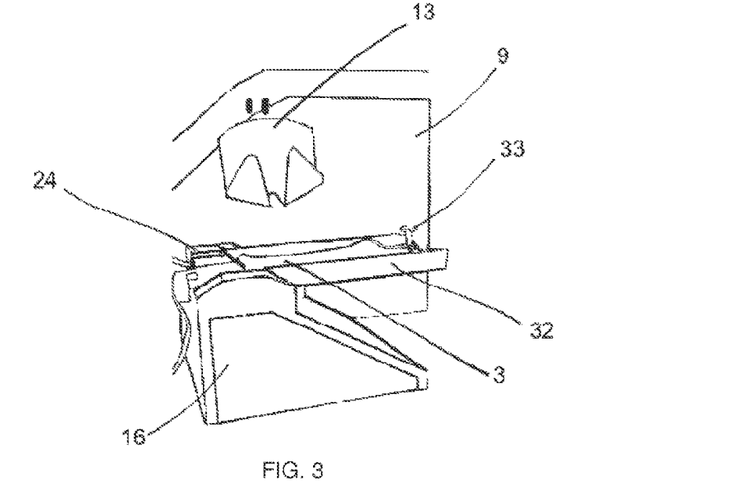
FIG. 3 diagrammatically shows a partial view and in perspective of a second embodiment of an apparatus according to the invention.

According to FIGS. 2 and 3, the apparatus 9 has the form of a case provided with supports 10, 11, 12 in order to place the various bags and filtration units of the system of bags on the apparatus. These devices are for example suspension hooks or plates.

In a particular embodiment shown in FIG. 3, the support 13 is intended to support the filtration unit of the system of bags (not shown in FIG. 3) and has the form of two parallel walls connected together by a curved bottom wall. The curved bottom wall has an opening that extends over one of the parallel walls. This opening is intended to allow the tube connected to the filtration unit to pass.

The apparatus 9 comprises:
an extraction device 14 intended for extracting the blood component by compressing the primary bag,
a control device 15 intended for enabling the transfer of said extracted component or of said extracted component and of the additive solution to the collecting satellite bag by the intermediary of tubes,
an agitation device 16 intended for agitating the collecting satellite bag, and
a drive system for commanding said extraction, control and agitation devices, said system being designed to enable the uniform mixing of the extracted blood component and of the additive solution in said collecting satellite bag 3.

According to an embodiment, the extraction device 14 comprises two vertical walls parallel to each other, between which the primary bag 1 is intended to be placed. At least one of the walls is mobile in translation in order to compress the primary bag 1 in order to extract the blood components and transfer them to the dedicated satellite bags 2, 3.

The control device 15 comprises a set of clamps 17, 18, 19, 20, 21 for the tubes connecting together the primary bag 1, the bag 4 of additive solution and the collecting satellite bag 3, respectively.

For example, the control device 15 comprises between one and six clamps. Each clamp is able to clamp a tube in order to block the fluid flow inside said tube.

In particular, the clamps make it possible to control the flow of separate components coming from the primary bag 1, the flow of the plasma to the satellite bag 2 for collecting plasma, the flow of the packed red blood cells to the satellite bag 3 for collecting packed red blood cells and the flow of the additive solution from the bag 4 of solution to the satellite bag 3 for collecting packed red blood cells.

In certain systems of bags, the additive solution is already present in the satellite bag 3 for collecting packed red blood cells. In this case, the satellite bag 3 for collecting packed red blood cells and the bag 4 of solution are confounded. The control device 15 then enables the transfer of an extracted component from the primary bag 1 to the collecting satellite bag 3 by the intermediary of tubes.

When the additive solution is contained in a bag 4 of solution, separate from the satellite bag 3 for collecting the component, the control device 15 enables the transfer of the extracted component from the primary bag 1 and of the additive solution to the satellite bag 3 for collecting the blood component.

In a particular example, the clamps 17, 18, 19, 20, 21 include a welder able to weld the tube in such a way as to definitively close off the flow in said tube, after extraction and transfer of the separated blood components into the appropriate bags.

According to another example, at least one of the clamps 17, 18, 19, 20, 21 comprises a flow regulator. This clamp 20 provided with a flow regulator in particular makes it possible to control the speed of the flow of plasma in the plasma bag. The regulation of the flow of plasma provides for the maintaining of the buffy coat in a substantially constant position in the primary bag during an extraction referred to as top & bottom, i.e., when the plasma and the packed red blood cells are extracted simultaneously from the primary bag 1 via the top and the bottom of the primary bag, respectively.

Each clamp 17, 18, 19, 20, 21 is furthermore provided with an optical detector in order to signal the proper positioning of the tube in the clamp.

According to another embodiment, the control device 15 comprises a set of devices 22, 23, 24 for breaking at least one closing element comprising a weak zone, said closing element being arranged inside one of the tubes connecting the primary bag, the bag of additive solution and the collecting satellite bag to one another, respectively.

For example, the control device comprises between one and four devices for breaking. These devices for breaking automate the method of extraction of blood components.

According to a particular embodiment, the apparatus is provided with three devices 22, 23, 24 for breaking: one 22 intended to break the closing element of the primary bag 1, the second 23 for the bag 4 of additive solution, and the third 24 for the satellite bag 3 for collecting packed red blood cells.

Alternatively, the device 24 for breaking makes it possible to simultaneously break two adjacent closing elements on a bag.

Figure 4:
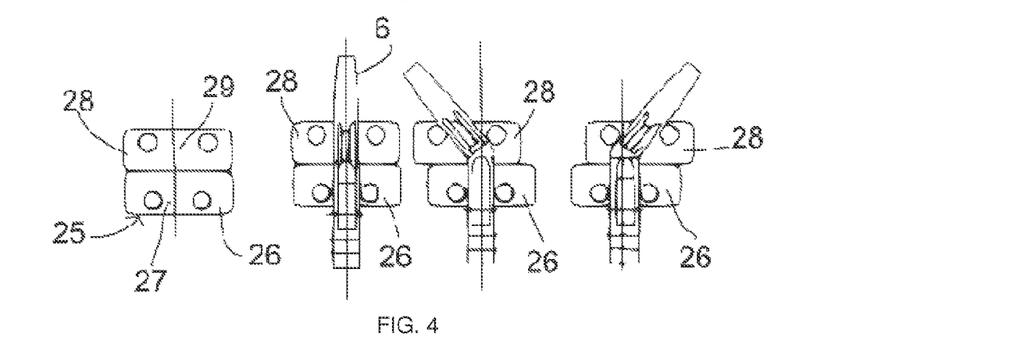
FIG. 4 diagrammatically shows the operation of a device for breaking a closing element.

According to FIG. 4, each one of said devices 22-24 for breaking comprises a set for receiving 25 of at least one tube, said set comprising a fixed element 26 provided with a first housing 27 intended to receive a first portion of said tube, a mobile element 28 provided with a second housing 29 intended to receive a second portion of said flexible tube, and a member for driving in displacement the mobile element 28, in such a way as to be able to cause the breaking of the weak zone of the closing element when the tube is placed in the set for receiving 25.

Figure 5:
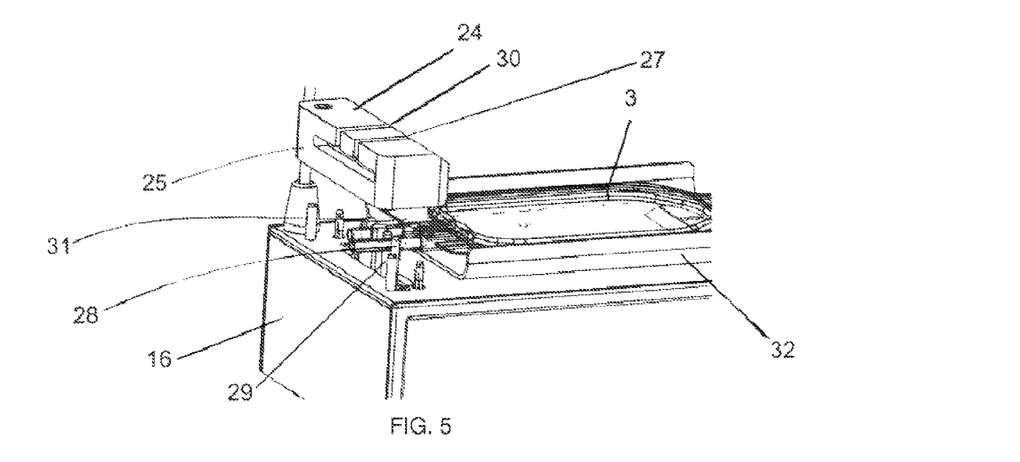
FIG. 5 diagrammatically shows a partial view and in perspective of a device for breaking included in an apparatus according to the invention.
Figure 6:
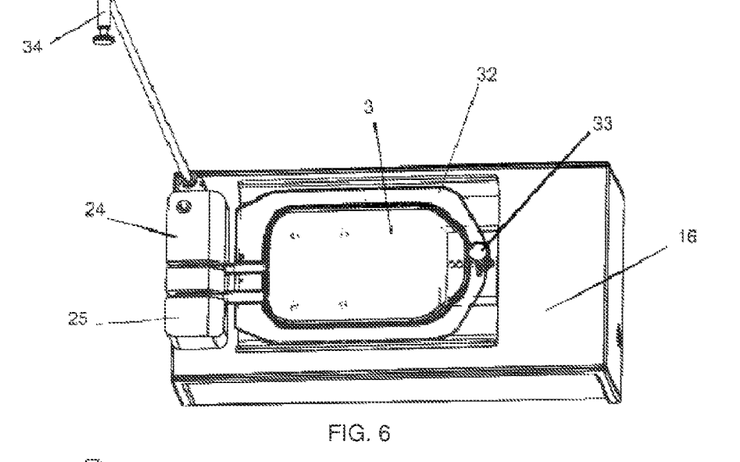
FIGS. 6 to 8 diagrammatically show a partial and exploded view of an agitation device of an apparatus according to a first embodiment of the invention.

In FIG. 5, the device for breaking 24 provides for the simultaneous breaking of two closing elements of a satellite bag 3 for collecting a blood component, the bag comprising two access channels arranged on the top of the bag. In this embodiment, the set for receiving 25 comprises a fixed element 26 provided with a first housing 27 and with a second housing 30, and a mobile element 28 provided with a first housing 29 and with a second housing 31 for tubes. The housings 28, 29 of the mobile element 28 are in the form of rods.

A more detailed description of such devices 22-24 for breaking can be found in document FR 2968 568.

The apparatus advantageously comprises a set of clamps 17-21 and a set of devices 22-24 for breaking.

According to the invention and in relation with FIGS. 6 to 11, the apparatus 9 comprises an agitation device 16 intended for agitating the satellite bag 3 for collecting the blood component.

The agitation device 16 comprises a mobile plate 32 whereon the collecting satellite bag 3 is intended to be placed. The plate 32 in particular comprises means 33 for maintaining the bag on the plate, such as for example a rod or a screw, introduced into a grommet or a slot of the bag.

Figure 8:
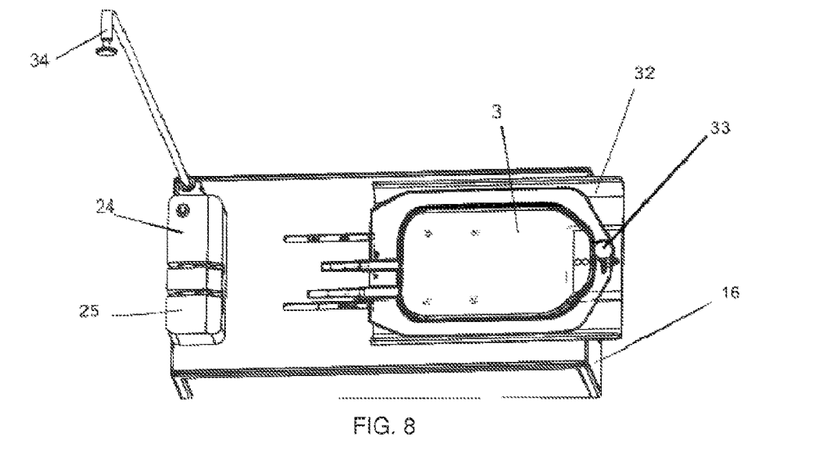
Figure 9:
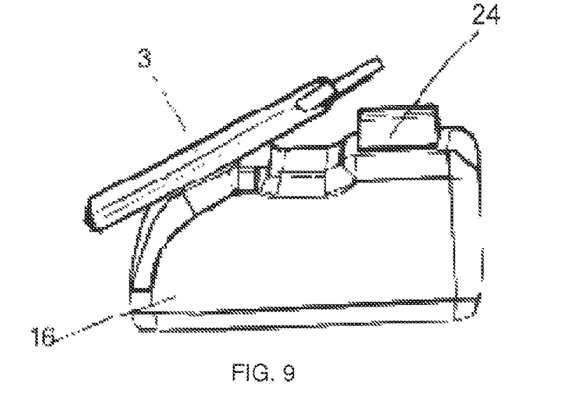
FIG. 9 diagrammatically shows a partial view of an agitation device of an apparatus according to a second embodiment of the invention.
Figure 10:
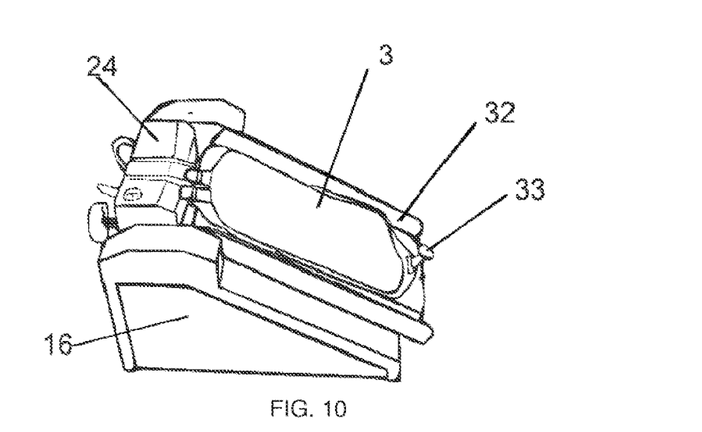
FIGS. 10 and 11 diagrammatically show a partial view of an agitation device of an apparatus according to a third embodiment of the invention.
Figure 11:
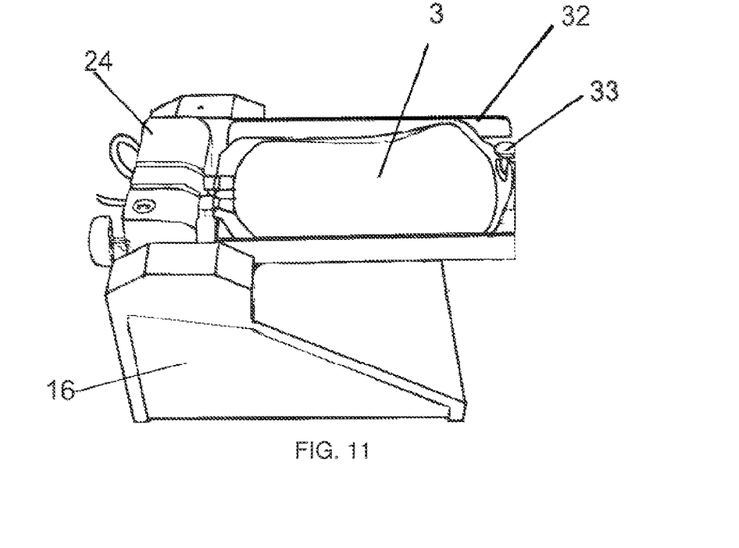

This plate 32 is mobile either according to a linear movement (FIGS. 6 to 8) and/or according to a movement of rotation (FIGS. 9 to 11).

When the movement is linear, the movement of the plate 32 is a back-and-forth movement, the collecting satellite bag 3 being placed horizontally.

Advantageously, the movement of the mobile plate 32 is a movement of rotation. This movement limits the length of tube required to provide for the movement.

According to FIG. 9, the axis of rotation of the mobile plate 32 is placed transversally to said plate, in particular in the vicinity or on the transversal axis of said plate.

Advantageously and as shown in FIGS. 10 and 11, the axis of rotation of the mobile plate 32 is placed transversally to said plate, in the vicinity of the front portion of the plate intended to receive the top of the collecting satellite bag 3.

Figure 7:
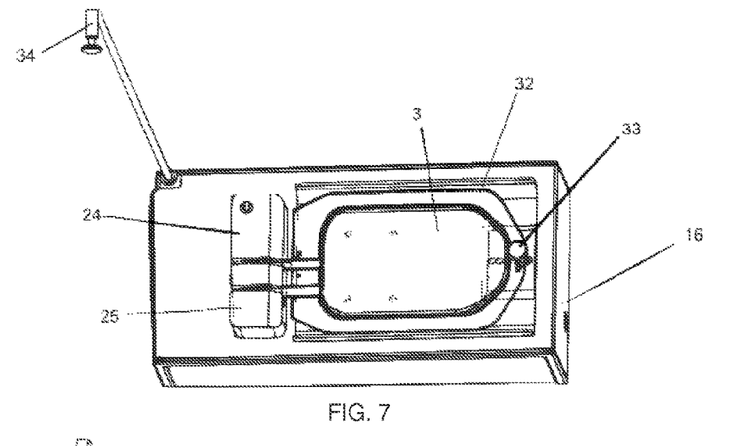

In the case wherein the control device 15 comprises a device 24 for breaking, the latter is connected to the mobile plate. As such, the collecting satellite bag 3 is maintained in place on the plate by at least said device for breaking 24 (FIG. 7).

Alternatively, the device for breaking 24 is fixed in relation to the mobile plate 32 and the agitation device 16 is arranged so that the collecting satellite bag 3 is mobile from a position wherein the closing element 7, 8 of the tube connected to said bag is in the set for receiving 25 of a device for breaking 24 (FIG. 6) to a position wherein said closing element 7, 8 is outside of said set for receiving 25 (FIG. 8). This embodiment is simpler to implement and more compact.

This particular movement of the agitation device 16 makes it possible to release the closing elements of the collecting satellite bag 3 from the device for breaking 24, before generating the movement of the plate 32.

In another particularly advantageous alternative shown in FIGS. 10 and 11, the device for breaking 24 is fixed and the plate 32 is mobile according to a movement of rotation wherein the axis of rotation is placed transversally to said plate, in the vicinity of the front portion of the plate 32 intended to receive the top of the collecting satellite bag 3, i.e. in the vicinity of the device for breaking 24. As such, no reserve of length of tube is required to provide for the movement of rotation and the bag is well maintained in place during the movement of the plate 32 by the device for breaking 24.

In a particular embodiment, the apparatus 9 further comprises a weighing device intended for weighing at least one bag, said primary bag, said collecting satellite bag or the bag of solution. The weighing device comprises a set of balances 34 of the primary bag, of the collecting satellite bag or of the bag of solution, respectively. This weighing device makes it possible to control on the one hand the proper separation of the components and on the other hand the proper breaking of the closing elements. For example, if a closing element of a bag was not broken correctly, the flow of fluid to or from this bag will not be possible and the weight of the bag will not be modified.

The apparatus 9 further comprises a set of optical detectors 35 placed at level of the primary bag 1 and/or of tubes in order to detect the interface between the various blood components and/or the passage of a component in the tubes.

The apparatus 9 is provided with a drive system in order to operate this. The drive system in particular commands said extraction 14, control 15 and agitation 16 devices.

The drive system notably comprises a microprocessor designed to execute a command programme. The execution of this programme enables the drive system to drive the extraction 14, control 15 and agitation 16 devices, according to for example signals received by the optical detectors and/or the weighing device.

The drive system is designed to enable the uniform mixing of the extracted blood component and of the additive solution in said collecting satellite bag 3.

For example, the drive system is able to command the extraction 14, control 15 and agitation 16 devices, in such a way as to transfer the additive solution to the collecting satellite bag 3 during the extraction of the blood component and to agitate said collecting satellite bag 3 during the transfer of the extracted blood component and of the additive solution to said collecting satellite bag 3.

In particular, for a system of bags such as shown in FIG. 1, the drive system executes the following actions:
  closure of the clamps 17, 18, 19, 20, 21,
  rupture of the closing elements of the various tubes 6, 7, 8,
  opening of the clamps 17, 18, 19, 20, 21 in order to enable the extraction of the blood components to the satellites bags 2, 3 and the flow of the additive solution to the collecting satellite bag 3,
  compression of the primary bag 1 containing the blood components separated beforehand by centrifugation, the compression driving the transfer of the plasma to a satellite bag 2 for collecting plasma and the transfer of the packed red blood cells to the satellite bag 3 for collecting red blood cells,
  agitation of the collecting satellite bag 3.

The drive system is advantageously designed to agitate the collecting satellite bag 3 during the compression of the primary bag 1 and/or to enable the simultaneous transfer of the blood component and of its additive solution to the collecting satellite bag 3 by suitably controlling the opening of the clamps 17-21 and the breaking of the closing elements 6-8.

As such, it is possible to obtain in an automated manner a uniform mixture of blood component and of additive solution by combining a technique of mixing and a technique of agitation. Indeed, a first mixing is produced by introducing at least partially simultaneously the additive solution and the blood component in the collecting satellite bag. The agitation using the agitation device then provides the uniformity of the mixture.

The apparatus 9 further comprises a user interface 36 that has in particular a viewing screen 37 and a keyboard 38.

According to a second aspect, the invention relates to a method for extracting at least one blood component contained in a primary bag 1 of a system of bags, using an apparatus 9 according to the first aspect of the invention, said method comprising the steps of:
  compressing the primary bag 1 in such a way as to extract the blood component from the primary bag and transfer it to the collecting satellite bag 3,
  transferring the additive solution from the bag 4 of solution to the collecting satellite bag 3 during the transfer of the extracted blood component to said collecting satellite bag 3, and
  agitating the collecting satellite bag 3 during the transfer of the extracted blood component and of the additive solution to said collecting satellite bag 3.

In particular, the blood component to be extracted is a packed red blood cells obtained via centrifugation of a unit of whole blood. Alternatively, the blood component is a platelet concentrate obtained via centrifugation of a pool of buffy coats.

The additive solution is a preservation solution such as those described hereinabove.

The system of bags used in this method comprises at least one primary bag 1, a bag 4 of solution containing an additive solution for said blood component and at least one collecting satellite bag 3 intended for collecting said blood component to which said additive solution has been added, said bags 1, 3, 4 being separate and connected to one another by tubes.

According to the system of bags used, the compression of the primary bag 1 enables the extraction of the blood components consecutively (top-top method) or simultaneously (top & bottom method). For the consecutive extraction of the blood components, the primary bag 1 is provided with an access channel at the top of the bag. For simultaneous extraction, the primary bag 1 has access channels at the top and the bottom of the bag (FIG. 1).

During the compression of the primary bag 1 and the transfer of the blood component to the collecting satellite bag 3, the method provides to transfer the additive solution to said collecting satellite bag 3. This transfer, at least partially simultaneously, of the additive solution and of the blood component provides an effective mixture of the two liquids.

According to an embodiment, the transfer of the additive solution to the collecting satellite bag 3 is carried out via gravity. In this case, the bag 4 of solution is simply suspended above the collecting satellite bag 3.

Advantageously, a filtration unit 5 is provided on the tube connecting the bag 4 of solution and the collecting satellite bag 3. As such, during the transfer of the additive solution to the collecting satellite bag 3, the additive solution passes through the filtration unit 5 arranged between the bag 4 of solution and the collecting satellite bag 3.

In a particular system of bags, the tube connecting the primary bag 1 and the collecting satellite bag 3 and the tube connecting the bag 4 of solution and the collecting satellite bag 3 comprise a common portion of tube connected by a Y-shaped connector. In this case, the extracted blood component and the additive solution are mixed with one another in said common portion of tube.

Alternatively, the additive solution and the extracted blood component are transferred into the collecting satellite bag 3 by two separate access channels of said collecting satellite bag 3.

The method according to the invention provides to agitate the collecting satellite bag 3 during the transfer of the extracted blood component and of the additive solution to said collecting satellite bag 3. The agitation is carried out according to a linear and/or rotation movement.

This agitation improves the uniformity of the mixture of blood component and of additive solution.

With the method of the invention, the extracted component and with the additive solution added, can then be filtered through a filtration unit 5, without an additional step of rendering the mixture uniform.

The invention claimed is:

1. An apparatus for extracting at least one blood component contained in a primary bag of a system of bags, said system of bags further comprising at least one bag of solution containing an additive solution for said blood component and at least one collecting satellite bag configured to collect said blood component to which said additive solution has been added, said bags being connected to one another by tubes, said apparatus comprising:
  an extraction device configured to extract the blood component by compressing the primary bag, and a control device configured to transfer said extracted component, or said extracted component and the additive solution, to the collecting satellite bag by the intermediary of tubes, further comprising:

an agitation device configured to agitate the collecting satellite bag, wherein the agitation device comprises a mobile plate whereon the collecting satellite bag is configured to be placed, said mobile plate being mobile according to a rotation movement along an axis of rotation placed transversally to said mobile plate and at the extremity thereof configured to receive a top of the collecting satellite bag; wherein the control device comprises a set of devices for breaking of at least one closing element, said devices for breaking configured so as to maintain said collecting satellite bag in place on the mobile plate during the movement of the mobile plate and a drive system configured to control said extraction device, said control device and said agitation device, said system being designed to enable the uniform mixing of the extracted blood component and of the additive solution in said collecting satellite bag.

2. The apparatus according to claim 1, wherein the control device comprises a set of clamps for the tubes connecting together the primary bag, the bag of additive solution and the collecting satellite bag, respectively.

3. The apparatus according to claim 1, wherein the set of devices for breaking of at least one closing element comprising a weak zone, said closing element being arranged inside one of the tubes connecting together the primary bag, the bag of additive solution and the collecting satellite bag, respectively.

4. The apparatus according to claim 3, wherein each one of said devices for breaking comprises a set for receiving of at least one tube, said set comprising a fixed element provided with a first housing intended to receive a first portion of said tube, a mobile element provided with a second housing configured to receive a second portion of said flexible tube, and a member for driving the mobile element in displacement, in such a way as to be able to cause the breaking of the weak zone of the closing element when the tube is placed in the set for receiving.

5. The apparatus according to claim 4, wherein the agitation device is arranged so that the collecting satellite bag is mobile from a position wherein the closing element of the tube connected to said bag is in the set for receiving of a device for breaking to a position wherein said closing element is outside of said set for receiving.

6. The apparatus according to claim 1, wherein said device comprises a weighing device intended to weigh at least one of the primary bag, the collecting satellite bag and the bag of solution.

7. The apparatus according to claim 1, wherein the drive system is able to command the extraction, control and agitation devices, in such a way as to transfer the additive solution to the collecting satellite bag during the extraction of the blood component and to agitate said collecting satellite bag during the transfer of the extracted blood component and of the additive solution to said collecting satellite bag.

8. A method for extracting at least one blood component contained in a primary bag of a system of bags, said system of bags further comprising at least one bag of solution containing an additive solution for said blood component and at least one collecting satellite bag configured to collect said blood component to which said additive solution has been added, using an apparatus according to claim 1, said method comprising the steps of:

placing the collecting satellite bag on the mobile plate of the agitation device in such a way to receive the top of the collecting satellite bag at the extremity of the mobile plate where the axis of rotation is placed, compressing the primary bag in such a way as to extract the blood component from the primary bag and transfer it to the collecting satellite bag, transferring the additive solution from the bag of solution to the collecting satellite bag during the transfer of the extracted blood component in said collecting satellite bag, agitating the collecting satellite bag during the transfer of the extracted blood component and of the additive solution in said collecting satellite bag by moving the mobile plate between a horizontal position and a sloped position wherein the extremity receiving the top of the collecting satellite bag is higher than an opposite extremity.

9. The method according to claim 8, wherein the transfer of the additive solution in the collecting satellite bag is carried out via gravity.

10. The method according to claim 8, wherein during the transfer of the additive solution to the collecting satellite bag, the additive solution passes through a filtration unit arranged between the bag of solution and the collecting satellite bag.

11. The method according to claim 8, wherein the additive solution and the extracted blood component are transferred to the collecting satellite bag by two separate access channels of said collecting satellite bag.

12. The method according to claim 8, wherein the blood component is a packed red blood cells obtained via centrifugation of a unit of whole blood.

13. An apparatus for extracting at least one blood component contained in a primary bag of a system of bags, said system of bags further comprising at least one bag of solution containing an additive solution for said blood component and at least one collecting satellite bag configured to collect said blood component to which said additive solution has been added, said bags being connected to one another by tubes, said apparatus comprising:

an extraction device configured to extract the blood component by compressing the primary bag, a control device configured to transfer said extracted component, or said extracted component and the additive solution, to the collecting satellite bag by the intermediary of tubes, said control device comprising a device for breaking at least one closing element arranged inside one of the tubes connecting the collecting satellite bag, said device for breaking comprising at least a set for receiving the portion of one of the tubes with the closing element arranged inside, an agitation device configured to agitate the collecting satellite bag, wherein said set for receiving is fixed, the agitation device further comprising a mobile plate whereon the collecting satellite bag is configured to be placed; the mobile plate being mobile according to a rotation movement along an axis of rotation placed transversally to the mobile plate, at the extremity thereof configured to receive a top of the collecting satellite bag and in the vicinity of the set for receiving; wherein the mobile plate is mobile between a horizontal position and a sloped position wherein the extremity configured to receive the top of the collecting satellite bag is higher than an opposite extremity; and a drive system configured to control said extraction device, said control device and said agitation device, said system being designed to enable the uniform mixing of the extracted blood component and of the additive solution in said collecting satellite bag.

14. A method for extracting at least one blood component contained in a primary bag of a system of bags, said system of bags further comprising at least one bag of solution containing an additive solution for said blood component and at least one collecting satellite bag configured to collect said blood component to which said additive solution has been added, said bags being connected to one another by tubes, using an apparatus according to claim 13, said method comprising the steps of:

placing the collecting satellite bag on the mobile plate of the agitation device in such a way to receive the top of the collecting satellite bag at the extremity of the mobile plate where the axis of rotation is placed,     placing one of the tubes with a closing element arranged inside and connecting the collecting satellite bag, into the device for breaking,     breaking the closing element arranged inside the tube connecting the collecting satellite bag,     compressing the primary bag in such a way as to extract the blood component from the primary bag and transfer it to the collecting satellite bag,     transferring the additive solution from the bag of solution to the collecting satellite bag during the transfer of the extracted blood component in said collecting satellite bag; and     agitating the collecting satellite bag during the transfer of the extracted blood component and of the additive solution in said collecting satellite bag by moving the mobile plate between a horizontal position and a sloped position wherein the extremity receiving the top of the collecting satellite bag is higher than an opposite extremity.

\* \* \* \* \*